US010751021B2

(12) United States Patent (10) Patent No.: US 10,751,021 B2
Vancamberg et al. (45) Date of Patent: Aug. 25, 2020

(54) SYSTEM AND METHOD FOR ACQUIRING AN X-RAY IMAGE

(71) Applicant: GENERAL ELECTRIC COMPANY, Schenectady, NY (US)

(72) Inventors: Laurence Vancamberg, Poissy (FR); Stephane Bedin, Paris (FR); Helene Daval, Buc (FR); Agnes Le Roux, Versailles (FR); Alexis Hubert, Buc (FR); Godfrain Jacques Kounkou, Vancouver (CA)

(73) Assignee: GENERAL ELECTRIC COMPANY, Schenectady, NY (US)

(*) Notice: Subject to any disclaimer, the term of this patent is extended or adjusted under 35 U.S.C. 154(b) by 71 days.

(21) Appl. No.: 16/227,464

(22) Filed: Dec. 20, 2018

(65) Prior Publication Data

US 2020/0196975 A1 Jun. 25, 2020

(51) Int. Cl.
*A61B 6/00* (2006.01)
*A61B 6/04* (2006.01)
*G06T 7/00* (2017.01)

(52) U.S. Cl.
CPC .............. *A61B 6/5294* (2013.01); *A61B 6/04* (2013.01); *A61B 6/502* (2013.01); *A61B 6/545* (2013.01); *G06T 7/0012* (2013.01); *G06T 2207/20084* (2013.01); *G06T 2207/30068* (2013.01)

(58) Field of Classification Search
CPC ......... A61B 6/5294; A61B 6/04; A61B 6/502; A61B 6/545; G06T 7/0012; G06T 2207/20084; G06T 2207/30068
USPC ...................................................... 378/37, 62
See application file for complete search history.

(56) References Cited

U.S. PATENT DOCUMENTS

7,440,600 B2 10/2008 Menhardt et al.
7,558,367 B1 7/2009 Tinwala et al.
7,796,793 B2 9/2010 Luo

*Primary Examiner* — Courtney D Thomas
(74) *Attorney, Agent, or Firm* — Grogan, Tuccillo & Vanderleeden, LLP (57) ABSTRACT

An x-ray imaging system is provided. The system includes an x-ray emitter and an x-ray detector. The system further includes a sensor operative to acquire one or more image acquisition factors, and a controller in electronic communication with the x-ray emitter, the x-ray detector, and the sensor. The controller is operative to: acquire an x-ray image of a patient via the x-ray emitter and the x-ray detector; receive the one or more image acquisition factors from the sensor; and generate a view name of the x-ray image based at least in part on the one or more image acquisition factors.

20 Claims, 9 Drawing Sheets

SYSTEM AND METHOD FOR ACQUIRING AN X-RAY IMAGE

BACKGROUND

Technical Field

Embodiments of the invention relate generally to medical imaging, and more specifically, to a system and method for acquiring an x-ray image.

DISCUSSION OF ART

X-ray based imaging systems acquire images of the internal structures of a patient by generating and transmitting x-rays through the patient, with the x-rays being subsequently received by a detector. Breast mammography machines are a type of x-ray based imaging system that are typically used to diagnostically image and/or biopsy a suspect lesion within a human breast. As will be understood, most mammography machines provide for a wide variety of different orientations/perspectives for imaging a breast, with the American College of Radiology ("ACR") setting a standard naming convention for the same.

Traditionally, an acquired x-ray image of a breast had to be manually inspected and labeled by medical personal. Manual inspection and labeling of x-ray images, however, was often a time-consuming process that was also prone to human error. Accordingly, many mammography machines now attempt to limit the amount of human involvement in labeling x-ray images with ACR standard names by providing pre-configured selectable options. For example, some mammography machines allow medical personal to select a view name from a pre-chosen list with exemplary graphics, e.g., simulated views corresponding to the selectable names. As will be understood, however, such a process remains susceptible to human error.

Additionally, many mammography machines are now capable of imaging biopsy samples immediately after they are acquired from a patient, as opposed to having to image the samples with a different apparatus. Such mammography machines, however, require human input to inform the machine that it will be imaging a biopsy sample, which usually requires different imaging parameters than those used to image a breast.

Further, some mammography machines are unable to detect the employment of various imaging accessories, e.g., magnifiers, biopsy tools, etc. As will be appreciated, the ability to automatically detect an imaging accessory during a mammogram is desirable.

What is needed, therefore, is an improved x-ray imaging system and method for acquiring an x-ray image.

BRIEF DESCRIPTION

In an embodiment, an x-ray imaging system is provided. The system includes an x-ray emitter and an x-ray detector. The system further includes a sensor operative to acquire one or more image acquisition factors, and a controller in electronic communication with the x-ray emitter, the x-ray detector, and the sensor. The controller is operative to: acquire an x-ray image of a patient via the x-ray emitter and the x-ray detector; receive the one or more image acquisition factors from the sensor; and generate a view name of the x-ray image based at least in part on the one or more image acquisition factors.

In another embodiment, an x-ray imaging system is provided. The system includes an x-ray emitter and an x-ray detector. The system further includes a sensor operative to acquire one or more image acquisition factors, and a controller in electronic communication with the x-ray emitter, the x-ray detector, and the sensor. The controller is operative to: receive the one or more image acquisition factors from the sensor; detect, based at least in part of the one or more image acquisition factors, that an x-ray image is to be of a biopsy sample of a patient; adjust one or more imaging parameters of the system based at least in part on the biopsy sample; and acquire the x-ray image via the x-ray emitter and the x-ray detector based at least in part on the one or more imaging parameters.

In still yet another embodiment, an x-ray imaging system is provided. The system includes an x-ray emitter and an x-ray detector. The system further includes an optical camera operative to acquire an optical image of a patient, and a controller in electronic communication with the x-ray emitter, the x-ray detector, and the optical camera. The controller is operative to: receive the optical image from the optical camera; generate a view name for an x-ray image of the patient via an artificial intelligence subsystem; and acquire the x-ray image via the x-ray emitter and the x-ray detector.

In still yet another embodiment, an x-ray imaging system is provided. The system includes an x-ray emitter and an x-ray detector. The system further includes an optical camera operative to acquire an optical image of a patient, and a controller in electronic communication with the x-ray emitter, the x-ray detector, and the sensor. The controller is operative to: receive the optical image from the sensor; and detect an imaging accessory within the optical image.

In still yet another embodiment, a non-transitory computer-readable medium storing instructions is provided. The stored instructions adapt a controller to: acquire an x-ray image of a patient via an x-ray emitter and an x-ray detector; receive one or more image acquisition factors from a sensor; and generate a view name of the x-ray image based at least in part on the one or more image acquisition factors.

DRAWINGS

The present invention will be better understood from reading the following description of non-limiting embodiments, with reference to the attached drawings, wherein below.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. Additionally, the terms "collide" and/or "collision", as used herein with respect to an imaging accessory (to include a biopsy apparatus) and an object to be imaged/biopsied, refer to a situation/scenario/event where a part of the imaging accessory distorts/contacts the matter/tissue of the object in an unexpected and/or undesirable manner.

Further, while the embodiments disclosed herein are described with respect to a breast imaging and/or biopsy system and procedure, it is to be understood that embodiments of the present invention may be applicable to other types of imaging and/or biopsy systems and procedures. Further still, as will be appreciated, embodiments of the present invention related imaging systems may be used to analyze tissue generally and are not limited to human tissue. Yet further sill, while the embodiments herein are disclosed as being directed towards x-ray imaging, it will understood that embodiments of the present invention may utilize other types of electromagnetic radiation.

Figure 1:
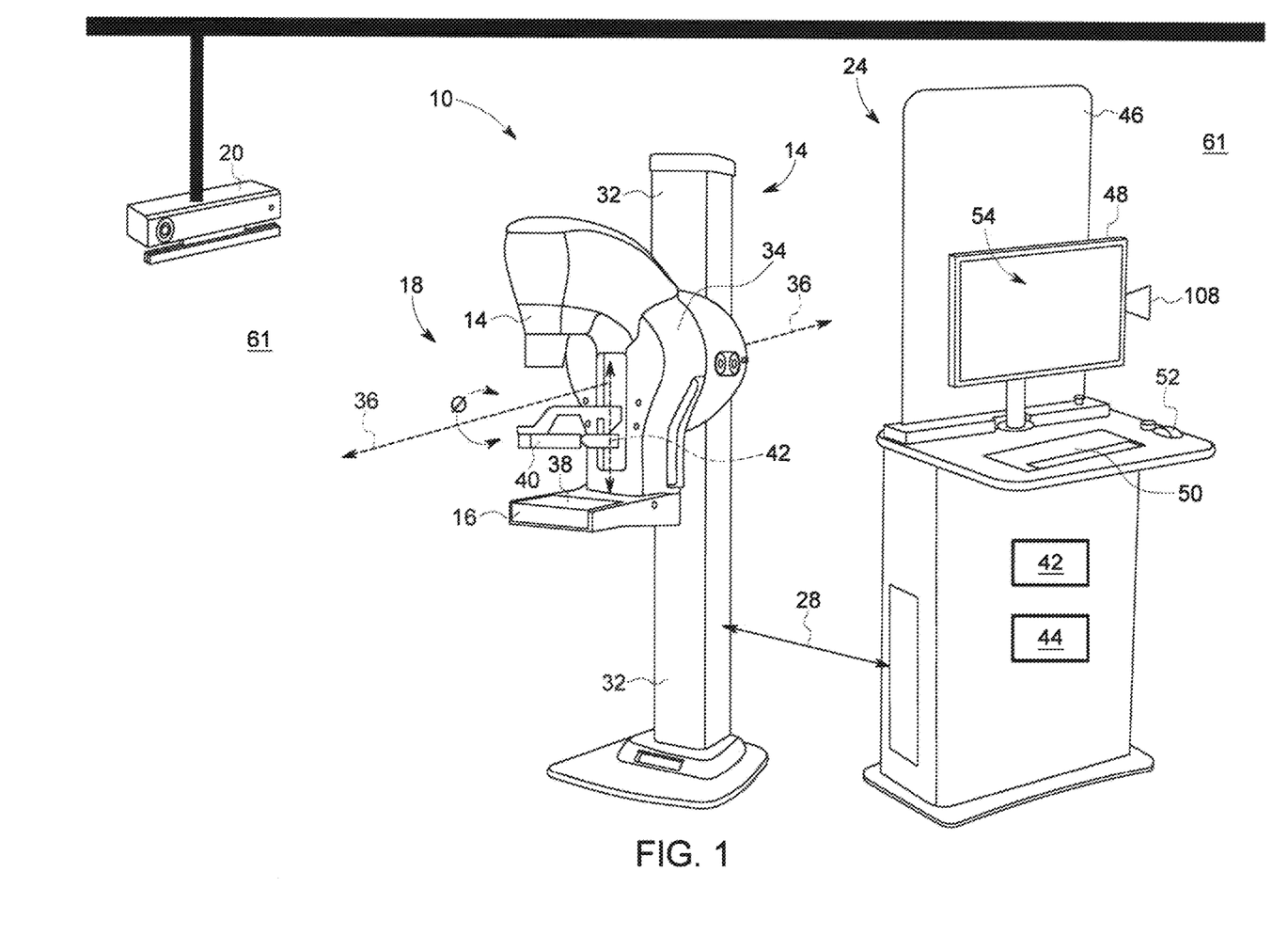
FIG. 1 is a perspective view of an x-ray imaging system for acquiring an x-ray image of a patient, in accordance with an embodiment of the present invention.

Referring now to FIG. 1, the major components of an x-ray imaging system 10 for acquiring x-ray images of a patient 12 (FIGS. 5-8), in accordance with an embodiment of the present invention, are shown. As will be appreciated, in embodiments, the system 10 includes an x-ray emitter 14 and an x-ray detector 16, which are disposed opposite of each other so as to collectively form an imaging device 18. While FIG. 1 depicts the imaging device 18 as part of a tomosynthesis mammography machine, it will be understood that, in embodiments, the imaging device 18 may be incorporated into, i.e., form part of, other types of imaging systems. As shown in FIG. 1, the system 10 further includes a sensor 20 operative to acquire one or more image acquisition factors 22 (FIG. 4), and a controller 24 in electronic communication with the x-ray emitter 14, the x-ray detector 16, and the sensor 20.

In operation, in accordance with an embodiment, the imaging device 18 obtains one or more x-ray images of the patient 12, i.e., emitter 14 transmits x-rays through the patient 12 which are received by the detector 16. The controller 24 electronically communicates with the imaging device 18, via data link 28, which may be a wired and/or wireless connection. In embodiments, the controller 24 is operative to acquire the x-ray images of the patient 12 via the emitter 14 and detector 16, to receive the one or more image acquisition factors 22 from the sensor 20, and to generate a view name 30 (FIG. 4) of the x-ray image based at least in part on the one or more image acquisition factors 22. The controller 24 may communicate with the emitter 14, detector 16 and/or sensor 20 via a wired and/or wireless data link, e.g., Wifi. The view name 30 may be an ACR compliant view name. As will be understood, in certain aspects, the controller 24 may not control the sensor 20, and still receive the acquisition factors 22, e.g., the controller that operates the sensor 20 may be different than the controller 24 that generates the view name 30.

As further shown in FIG. 1, the x-ray emitter 14 may be selectively adjustable between one or more positions, e.g., the x-ray emitter 14 may be mounted to a stand/support 32 via a rotatable mount 34 such that the x-ray emitter 14 rotates about a longitudinal axis 36. The x-ray detector 16 is operative to receive the x-rays and has a surface 38. In embodiments, the imaging device 18 may include one or more paddles 40, e.g., a compression plate, mounted to the stand 32 and slidably adjustable along axis 42 (and/or other axis/direction) so as to compress and/or restrain a part of the patient 12, e.g., a breast, against the surface 38.

The controller 24 may be a workstation having at least one processor/CPU 42 and a memory device 44. In other embodiments, the controller 24 may be embedded/integrated into one or more of the various components of the system 10 disclosed above. In embodiments, the controller 24 may be in further electrical communication with the paddle 40, and/or a biopsy apparatus 46 (FIG. 11) via link 28. In embodiments, the controller 24 may include a radiation shield 46 that protects an operator of the system 10 from the x-rays rays emitted by the x-ray emitter 14. The controller 24 may further include a display 48, a keyboard 50, mouse 52, and/or other appropriate user input devices, that facilitate control of the system 10 via a user interface 54, e.g., a GUI.

Figure 2:
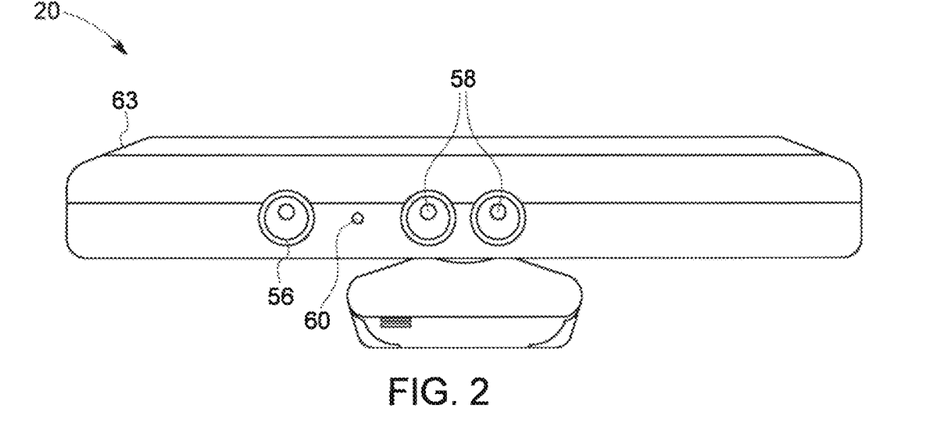
FIG. 2 is a diagram of a sensor of the x-ray imaging system of FIG. 1, in accordance with an embodiment of the present invention.
Figure 3:
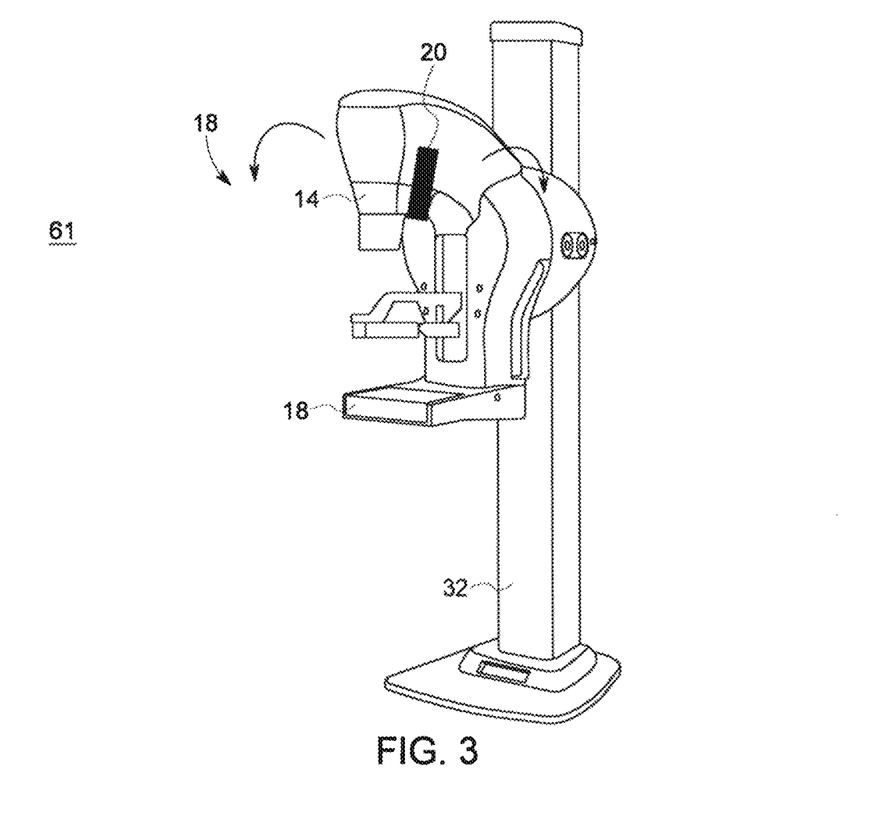
FIG. 3 is a diagram of an imaging device of the x-ray system of FIG. 1, in accordance with an embodiment of the present invention.

Turning to FIG. 2, the sensor 20 may include one or more of an optical camera 56, a depth camera 58, a thermal imaging camera 60, and/or other suitable sensors, e.g., pressure sensors, temperature sensors, lasers, etc. The sensor 20 may be disposed at a distance from the emitter 14 and detector 16 (as shown in FIG. 1), or incorporated into at least one of the emitter 14 and the detector 16 (as shown in FIG. 3), or any other component of the system 10. The sensor 20, and/or cameras 56, 58 and 60, are operative to acquire images of the patient 12, medical personnel/operator 70 (FIG. 5) and/or the room/scene 61 (FIGS. 1 and 3), e.g., the environment/room within which the system 10 is disposed. The optical camera 56 may be a red-green-blue ("RGB") camera, and the depth camera 58 may be a stereoscopic camera and/or an infrared projector coupled with an infrared camera. The cameras 56, 58 and 60 may be disposed within the same housing 63 or disposed apart from one another.

Figure 4:
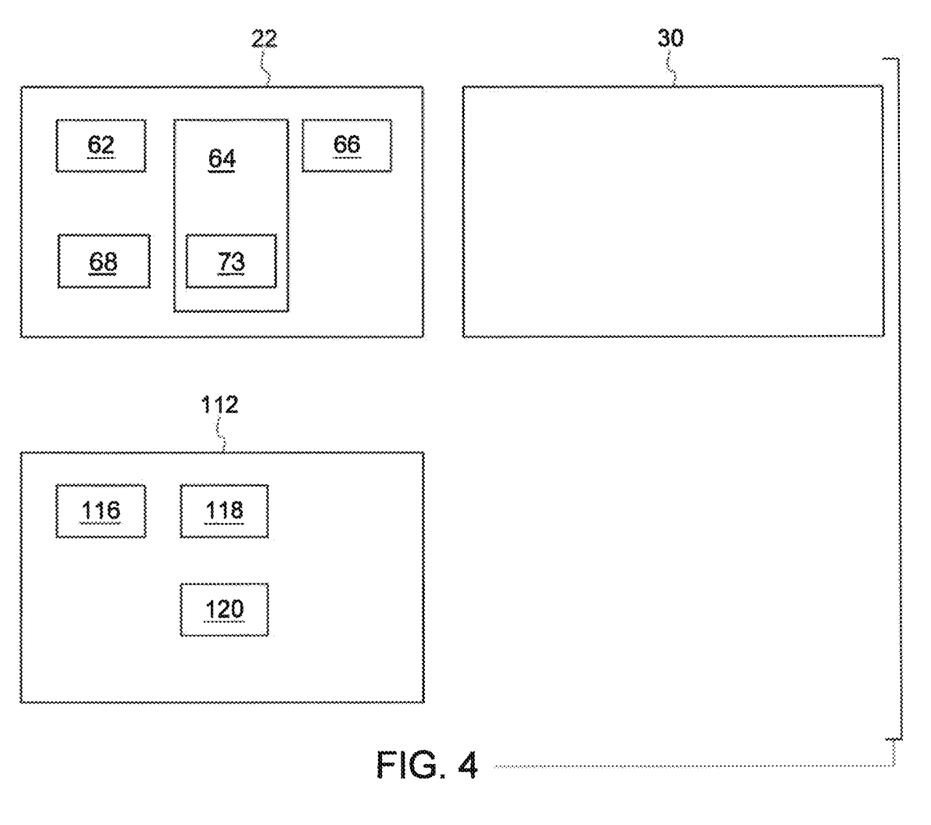
FIG. 4 is a diagram depicting image acquisition factors acquired by the x-ray imaging system of FIG. 1, and imaging parameters and a view name generated by the x-ray imaging system, in accordance with an embodiment of the present invention.
Figure 5:
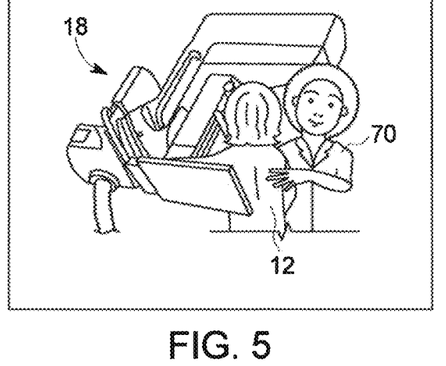
FIG. 5 is a diagram of a patient in a standing position with respect to the x-ray imaging system of FIG. 1, in accordance with an embodiment of the present invention.
Figure 6:
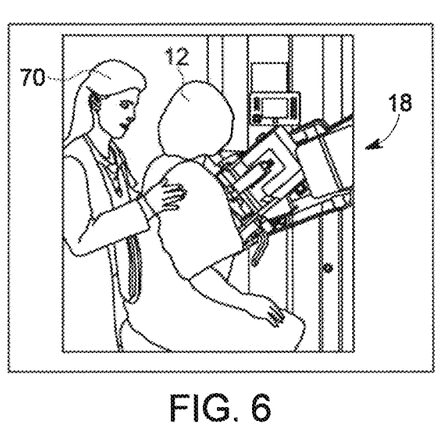
FIG. 6 is a diagram of a patient in a sitting position with respect to the x-ray imaging system of FIG. 1, in accordance with an embodiment of the present invention.
Figure 7:
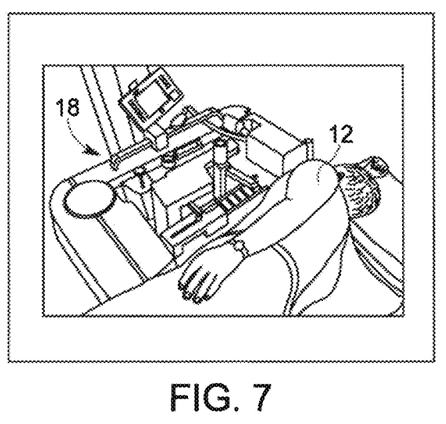
FIG. 7 is a diagram of a patient in a recumbent position with respect to the x-ray imaging system of FIG. 1, in accordance with an embodiment of the present invention.

Moving to FIG. 4, the imaging acquisition factors 22 may include a morphology 62 of the patient 12, a position 64 of the patient 12, a scene analysis 66, a gesture 68 of a medical operator/technologists 70 (FIGS. 5-6 and 8), and/or other factors suitable for determining the view name 30. As used herein with respect to a patient 12, the term "morphology" means a detected shape of a patient 12. The controller 24 may be operative to determine the position 64 of the patient 12 as being one of standing (FIG. 5), sitting (FIG. 6) or recumbent (FIG. 7). As used herein, the term "scene analysis" refers to a detected semantic context of an image captured by the sensor 20 based at least in part on one or more of the following features within the captured image: the orientation and/or location of the patient 12, the orientation and/or location of medical operators 70, and/or the orientation and/or location of pieces of equipment, e.g., the imaging device 18, biopsy apparatus 46, a chair, bed, etc. The gesture 68 of a medical operator 70 may be a hand signal, e.g., thumbs up, a body position, e.g., extended arm, or other suitable movement which can be detected by the sensor 20, and, in certain aspects, may be pre-saved in the memory device 44. In other words, the system 10 may be configured to recognize specific gestures as corresponding to particular view names 30.

Figure 8:
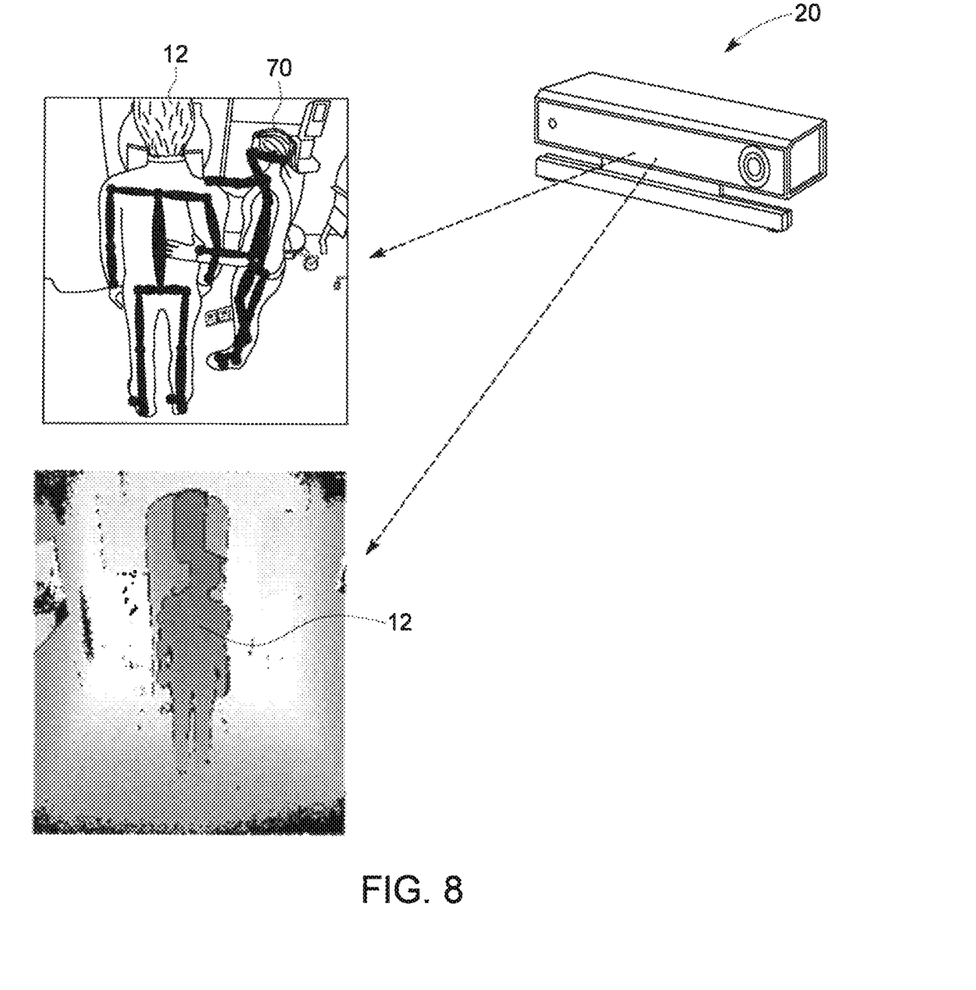
FIG. 8 is a diagram of the acquisition of one or more images by a sensor of the x-ray imaging system of FIG. 1, in accordance with an embodiment of the present invention.
Figure 9:
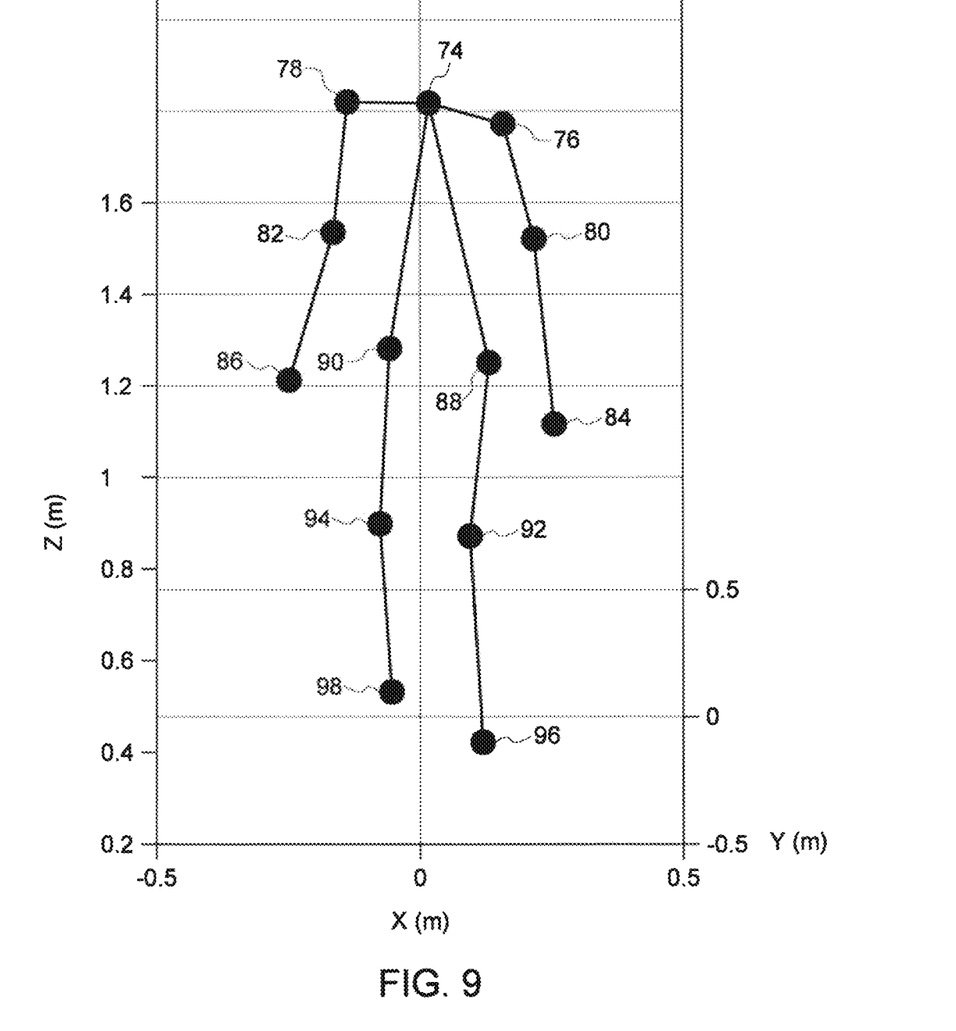
FIG. 9 is a diagram of key points of the patient and/or a medical operator detected by a controller of the x-ray imaging system of FIG. 1, based at least in part on the one or more images of FIG. 8, in accordance with an embodiment of the present invention.

As shown in FIGS. 8 and 9, the controller 24 may determine the position 64 (FIG. 4) of the patient 12 and/or medical operator 70 by detecting, via the sensor 20, one or more key points, e.g., the head 74, shoulders 76 and 78, elbows 80 and 82, hands 84 and 86, hips 88 and 90, knees 92 and 94, and/or feet 96 and 98 of either the patient 12 and/or medical operator 70. The controller 24 may then register the key points to a known location of the imagine device 18. In other words, the controller 24 may determine the location in 3D space of the key points with respect to the known location of the imaging device 18. The controller 24 may also locate and track a center of gravity, e.g., a center position between the detected hips 88 and 90 of a patient 12, via the depth camera 58 in regard to the x-ray detector 16. The controller 24 may also employ various key point algorithms, e.g., 2D algorithms when only RGB images are available, and 3D algorithms when RGB images and depth information are available, to extract features and determine the laterality of a body part of the patient 12, e.g., left vs right shoulder angles, torso angles, arm position, etc. In order to abstract depth information, the controller 24 may acquire a first reference frame from the depth camera 58 and differentiate, e.g., subtraction, it with a second frame from the depth camera 58, which in turn, provides for the assignment of depth coordinates for any moving objects, e.g., humans, within the field of view of the depth camera 58. In embodiments, the controller 24 may further build a depth model which may be used by the controller 24 to track and/or predict the position and/or orientation of the patient 12, medical operator 70 and/or other objects of interest within the scene 61.

In embodiments, generation of the view name 30 by the controller 24 may be further based at least in part on system 10 information, e.g., a rotation angle θ (FIG. 1) of the x-ray emitter 14 and/or detector 16 about the axis 36; the type of breast support (e.g., a MAG support 104 (FIG. 12)) or the type of paddle 40 (e.g., a SPOT paddle) used to acquire the x-ray image. In embodiments, generation of the view name 30 by the controller 24 may be further based at least in part on breast content information, e.g., implant suffix, which may be entered into the system 10 via GUI 54 by an operator 70. In embodiments, the GUI 54 may further provide for the medical operator 70 to inform the controller 24 that the image to be acquired by the imaging device 18 is an exaggerated view.

Figure 11:
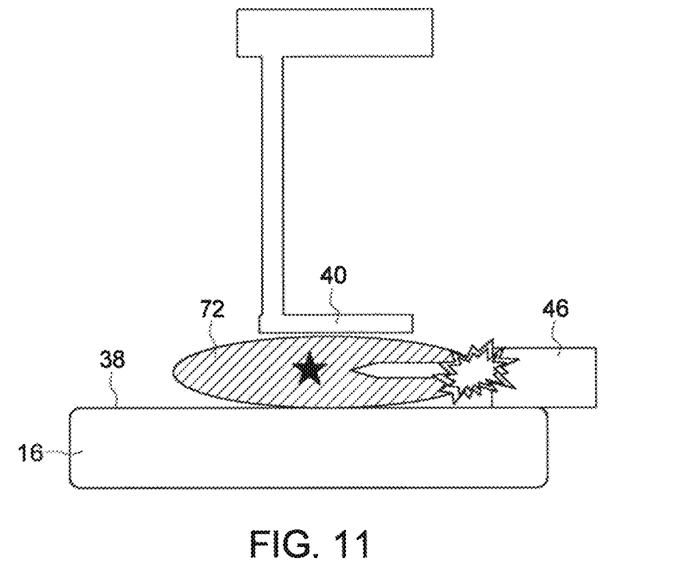
FIG. 11 is diagram of a biopsy apparatus of the x-ray imaging system of FIG. 1, in accordance with an embodiment of the present invention.

Referring again briefly to FIG. 4, the patient position 64 may further include a position 73 of a breast 72 (FIG. 11). For example, in embodiments, the controller 24 may determine a laterality of the breast 72, i.e., which of the left or right breast is being imaged. As will be understood, the sensor 20 may further provide for the controller 24 to detect whether a medical operator 70 is manipulating/shaping the breast of the patient 12, e.g., pulling, pressing, and/or rolling; and/or for the controller 24 to detect the axillary tail of the breast 72.

Figure 10:
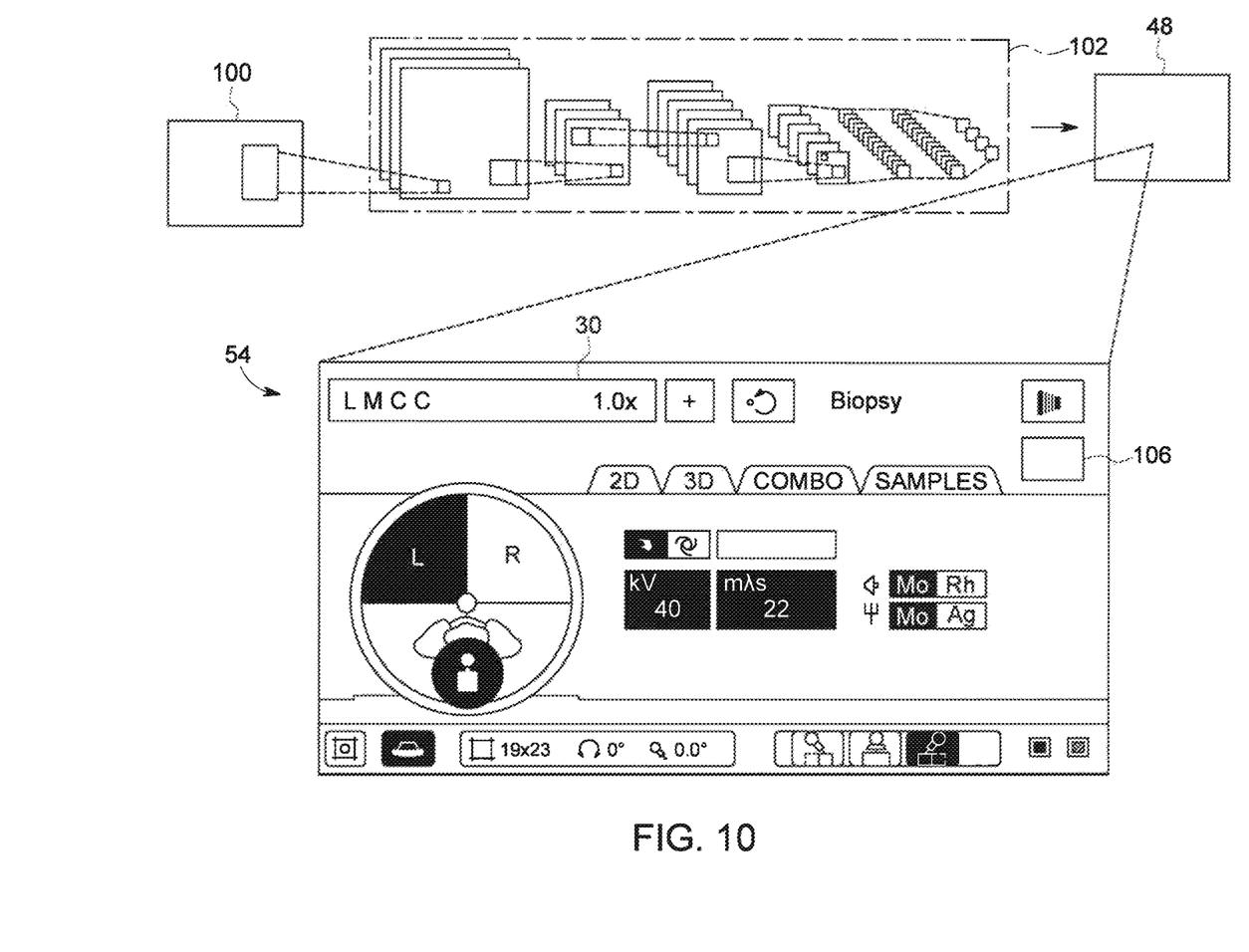
FIG. 10 is a diagram of a convolutional neural network and a graphical user interface ("GUI") of the x-ray imaging system of FIG. 1, in accordance with an embodiment of the present invention.

Referring now to FIG. 10, in embodiments wherein the sensor 20 includes an optical camera 56, an optical image 100 acquired by the optical camera 56 may be analyzed/processed by an artificial intelligence subsystem 102, which in turn, generates the view name 30. For example, in embodiments, the view name 30 may be generated by a convolutional neural network 102. The neural network 102 may be trained to associate certain features, e.g., patient 12 and/or medical operator 70 position/orientation, etc., within the images acquired by the cameras 56, 58 and/or 60, and optionally with additional system 10 information, with a particular view name 30, laterality and/or patient position.

Figure 12:
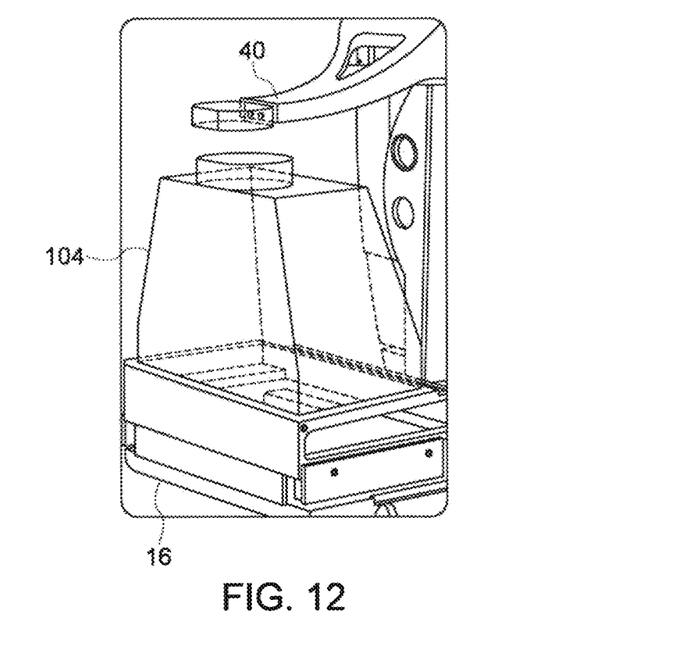
FIG. 12 is a diagram of a magnifier of the x-ray imaging system of FIG. 1, in accordance with an embodiment of the present invention.

Moving to FIGS. 11 and 12, in embodiments, the controller 24, via the sensor 20, may be operative to detect an imaging accessory, e.g., a biopsy apparatus/device 46 (FIG. 11), a magnifier 104 (FIG. 12), a paddle 40 (FIGS. 11 and 12), and/or a spacer, e.g., a device that raises a breast 72 off of the surface 38 of the detector 16. As used herein, the terms "biopsy apparatus" and "biopsy device" refer to mechanical apparatus that positions and/or guides a biopsy needle to a target sample site. In such embodiments, the controller 24 may be further operative to generate a collision indicator/indication, e.g., a message box and/or icon 106 (FIG. 10) on the GUI 54 and/or an audio sound/alarm 108 (FIG. 1). In embodiments, the GUI 54 may provide for the selection of a type of exam, a system configuration, and/or detection of user error, e.g., misalignment of the patient in accordance with a selected view type.

Figure 13:
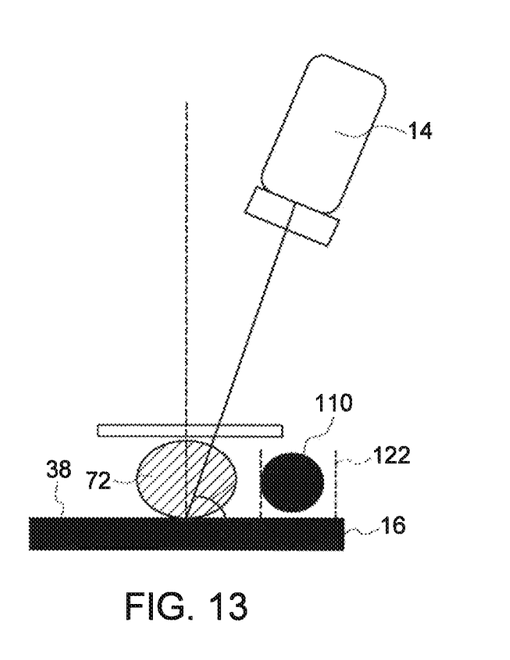
FIG. 13 is a diagram depicting a side profile view of a biopsy sample being imaged by the x-ray imaging system of FIG. 1, in accordance with an embodiment of the present invention.
Figure 14:
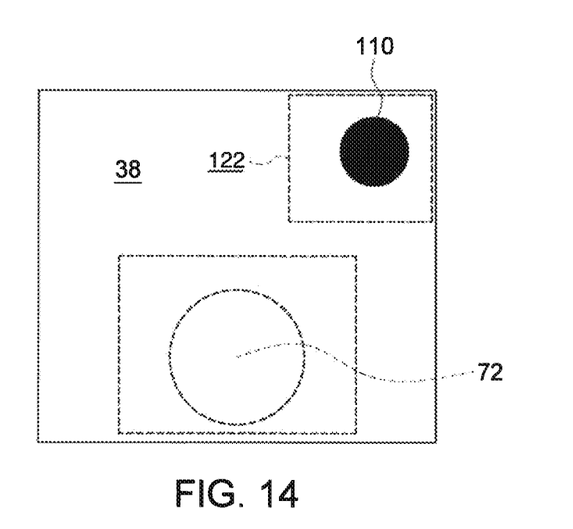
FIG. 14 is a diagram depicting a top-down view of the biopsy sample of FIG. 13 being imaged by the x-ray imaging system of FIG. 1, in accordance with an embodiment of the present invention.

As illustrated in FIGS. 13 and 14, in embodiments, the controller 24 may be operative to detect, based at least in part on one or more of the image acquisition factors 22, that the x-ray image to be acquired by the imaging device 18 is of a biopsy sample 110. In such embodiments, the controller 24 may be further operative to adjust one or more imaging parameters 112 (FIG. 4), e.g., the intensity 116 (FIG. 4) of the x-ray beam emitted by the x-ray emitter 14, the sensitivity 118 (FIG. 4) of the x-ray detector 16, the lenses/filters 120 (FIG. 4) used by the imaging device 18, and/or other adjustable parameters of the imaging device 18 prior to imaging of the biopsy sample 110. In such embodiments, the controller 24 may detect the biopsy sample 110 by detecting a border/edge of the biopsy sample 110 and/or a corresponding receiver/container/box 122 (FIG. 14). In such embodiments, the detection of the biopsy sample 110 and/or receiver 122 may be an acquisition factor 22.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment of the present invention, an x-ray imaging system is provided. The system includes an x-ray emitter and an x-ray detector. The system further includes a sensor operative to acquire one or more image acquisition factors, and a controller in electronic communication with the x-ray emitter, the x-ray detector, and the sensor. The controller is operative to: acquire an x-ray image of a patient via the x-ray emitter and the x-ray detector; receive the one or more image acquisition factors from the sensor; and generate a view name of the x-ray image based at least in part on the one or more image acquisition factors. In certain embodiments, the sensor includes an optical camera. In certain embodiments, the sensor further includes a depth camera. In certain embodiments, the sensor further includes a thermal imaging camera. In certain embodiments, the imaging acquisition factors include at least one of: a morphology of the patient; a position of the patient; a scene analysis; and a gesture performed by a medical staff member. In certain embodiments, the patient position is at least one of: standing; sitting; and recumbent. In certain embodiments, the position of the patient is a position of a breast of the patient. In certain embodiments, the controller generates the view name based at least in part on an artificial intelligence subsystem. In certain embodiments, the sensor is mounted at a distance from the x-ray emitter and the x-ray detector. In certain embodiments, the view name is based on: a breast laterality; a rotation angle of the x-ray emitter; and a position of the patient.

Other embodiments provide for an x-ray imaging system. The system includes an x-ray emitter and an x-ray detector. The system further includes a sensor operative to acquire one or more image acquisition factors, and a controller in electronic communication with the x-ray emitter, the x-ray detector, and the sensor. The controller is operative to: receive the one or more image acquisition factors from the sensor; detect, based at least in part of the one or more image acquisition factors, that an x-ray image is to be of a biopsy sample of a patient; adjust one or more imaging parameters of the system based at least in part on the biopsy sample; and acquire the x-ray image via the x-ray emitter and the x-ray detector based at least in part on the one or more imaging parameters. In certain embodiments, the sensor includes an optical camera. In certain embodiments, the sensor further includes a depth camera. In certain embodiments, the sensor further includes a thermal imaging camera. In certain embodiments, the imaging acquisition factors include at least one of: detection of a biopsy sample; detection of a biopsy sample receiver; and a scene analysis.

Yet still other embodiments provide for an x-ray imaging system. The system includes an x-ray emitter and an x-ray detector. The system further includes an optical camera operative to acquire an optical image of a patient, and a controller in electronic communication with the x-ray emitter, the x-ray detector, and the optical camera. The controller is operative to: receive the optical image from the optical camera; generate a view name for an x-ray image of the patient via an artificial intelligence subsystem; and acquire the x-ray image via the x-ray emitter and the x-ray detector. In certain embodiments, the artificial intelligence subsystem is a convolutional neural network.

Yet still other embodiments provide for an x-ray imaging system. The system includes an x-ray emitter and an x-ray detector. The system further includes an optical camera operative to acquire an optical image of a patient, and a controller in electronic communication with the x-ray emitter, the x-ray detector, and the sensor. The controller is operative to: receive the optical image from the sensor; and detect an imaging accessory within the optical image. In certain embodiments, the imaging accessory is at least one of: a magnifier; and a biopsy device. In certain embodiments, the controller is further operative to generate at least one of a collision indicator and a user error indicator based at least in part on the imaging accessory.

Yet still other embodiments provide for a non-transitory computer-readable medium storing instructions. The stored instructions adapt a controller to: acquire an x-ray image of a patient via an x-ray emitter and an x-ray detector; receive one or more image acquisition factors from a sensor; and generate a view name of the x-ray image based at least in part on the one or more image acquisition factors.

Accordingly, as will be appreciated, by automatically determining/generating a view name based on information acquired from various types of cameras and/or other sensors, some embodiments of the present invention reduce the amount of human dependencies in properly labeling an acquired x-ray image with the correct view name. Such a reduction in human dependencies often improves the accuracy of the labeling process, and in turn, provides for an x-ray imaging system with improved efficiencies over traditional designs.

Further, the automatic detection/generation of a view name based on information acquired from various types of cameras and/or other sensors, by some embodiments of the present invention, reduces the amount of contact between the x-ray imaging system and an operator of the system, which, as will be understood, improves cleanliness in a medical environment.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. An x-ray imaging system comprising:
   an x-ray emitter and an x-ray detector;
   a sensor operative to acquire one or more image acquisition factors;
   a controller in electronic communication with the x-ray emitter, the x-ray detector, and the sensor and operative to:
   acquire an x-ray image of a patient via the x-ray emitter and the x-ray detector;
   receive the one or more image acquisition factors from the sensor; and
   generate a view name of the x-ray image based at least in part on the one or more image acquisition factors.

2. The system of claim 1, wherein the sensor includes an optical camera.

3. The system of claim 2, wherein the sensor further includes a depth camera.

4. The system of claim 3, wherein the sensor further includes a thermal imaging camera.

5. The system of claim 1, wherein the imaging acquisition factors include at least one of:
   a morphology of the patient;
   a position of the patient;
   a scene analysis; and
   a gesture performed by a medical staff member.

6. The system of claim 5, wherein the patient position is at least one of:
   standing;
   sitting; and
   recumbent.

7. The system of claim 5, wherein the position of the patient is a position of a breast of the patient.

8. The system of claim 1, wherein the controller generates the view name based at least in part on an artificial intelligence subsystem.

9. The system of claim 1, wherein the sensor is mounted at a distance from the x-ray emitter and the x-ray detector.

10. The system of claim 1, wherein the view name is based on:
    a breast laterality;
    a rotation angle of the x-ray emitter; and
    a position of the patient.

11. An x-ray imaging system comprising:
    an x-ray emitter and an x-ray detector;
    a sensor operative to acquire one or more image acquisition factors;
    a controller in electronic communication with the x-ray emitter, the x-ray detector, and the sensor and operative to:
    receive the one or more image acquisition factors from the sensor;
    detect, based at least in part of the one or more image acquisition factors, that an x-ray image is to be of a biopsy sample of a patient;
    adjust one or more imaging parameters of the system based at least in part on the biopsy sample; and
    acquire the x-ray image via the x-ray emitter and the x-ray detector based at least in part on the one or more imaging parameters.

12. The system of claim 11, wherein the sensor includes an optical camera.

13. The system of claim 12, wherein the sensor further includes a depth camera.

14. The system of claim 13, wherein the sensor further includes a thermal imaging camera.

15. The system of claim 11, wherein the imaging acquisition factors include at least one of:
   detection of a biopsy sample;
   detection of a biopsy sample receiver; and
   a scene analysis.

16. An x-ray imaging system comprising:
   an x-ray emitter and an x-ray detector;
   an optical camera operative to acquire an optical image of a patient;
   a controller in electronic communication with the x-ray emitter, the x-ray detector, and the optical camera and operative to:
   receive the optical image from the optical camera;
   generate a view name for an x-ray image of the patient via an artificial intelligence subsystem; and
   acquire the x-ray image via the x-ray emitter and the x-ray detector.

17. The system of claim 16, wherein the artificial intelligence subsystem is a convolutional neural network.

18. An x-ray imaging system comprising:
   an x-ray emitter and an x-ray detector;
   an optical camera operative to acquire an optical image of a patient;
   a controller in electronic communication with the x-ray emitter, the x-ray detector, and the sensor and operative to:
   receive the optical image from the sensor; and
   detect an imaging accessory within the optical image.

19. The system of claim 18, wherein the controller is further operative to:
   generate at least one of a collision indicator and a user error indicator based at least in part on the imaging accessory.

20. A non-transitory computer-readable medium storing instructions that adapt a controller to:
   acquire an x-ray image of a patient via an x-ray emitter and an x-ray detector;
   receive one or more image acquisition factors from a sensor; and
   generate a view name of the x-ray image based at least in part on the one or more image acquisition factors.

* * * * *